(12) United States Patent
Tepic et al.

(10) Patent No.: US 9,737,349 B2
(45) Date of Patent: Aug. 22, 2017

(54) TIBIAL TUBEROSITY ADVANCEMENT CAGE FOR ACL INJURIES

(71) Applicant: KYON AG, Zurich (CH)

(72) Inventors: Slobodan Tepic, Zurich (CH); Joop Hopmans, Roden (NL)

(73) Assignee: KYON AG, Zurich (CH)

( * ) Notice: Subject to any disclaimer, the term of this patent is extended or adjusted under 35 U.S.C. 154(b) by 108 days.

(21) Appl. No.: 14/403,842

(22) PCT Filed: May 30, 2013

(86) PCT No.: PCT/IB2013/001577
§ 371 (c)(1),
(2) Date: Nov. 25, 2014

(87) PCT Pub. No.: WO2013/179142
PCT Pub. Date: Dec. 5, 2013

(65) Prior Publication Data
US 2016/0128748 A1 May 12, 2016

Related U.S. Application Data

(60) Provisional application No. 61/653,077, filed on May 30, 2012.

(51) Int. Cl.
*A61F 2/38* (2006.01)
*A61B 17/80* (2006.01)
(52) U.S. Cl.
CPC .......... *A61B 17/8095* (2013.01); *A61F 2/38* (2013.01); *F04C 2270/041* (2013.01)
(58) Field of Classification Search
CPC ........................................ A61F 2/38

USPC ............... 623/17.17–17.19, 20.32–20.34, 623/21.11–21.19; 606/90
See application file for complete search history.

(56) References Cited

U.S. PATENT DOCUMENTS

| | | | |
|---|---|---|---|
| 4,245,359 A * | 1/1981 | Stuhmer | A61F 2/30723 606/95 |
| 4,878,915 A * | 11/1989 | Brantigan | A61B 17/1604 606/247 |
| 5,669,909 A * | 9/1997 | Zdeblick | A61B 17/1671 606/247 |
| 5,879,403 A * | 3/1999 | Ostiguy | A61F 2/30723 623/23.48 |

(Continued)

FOREIGN PATENT DOCUMENTS

EP 2 452 641 5/2012

*Primary Examiner* — Yashita Sharma
(74) *Attorney, Agent, or Firm* — Occhiuti & Rohlicek LLP

(57) ABSTRACT

Methods and implants to treat anterior cruciate ligament (ACL) injuries are disclosed. The methods involve advancing the insertion of the patellar tendon to the proximal tibia by means of a partial osteotomy and a wedge-shaped cage (30). The wedge-shaped cage is specifically designed to facilitate transfer of not only compressive loads, but also of shear loads due to pull by the patellar tendon at its insertion to the tibial tuberosity. The cage decreases the angle between the patellar tendon and the common tangent plane formed by the condyles of the femur and the condyles of the tibia (sometimes called tibial plateau) and consequently modifies the internal joint force, restoring stability to the joint even if the ACL is ruptured. The methods and implants are applicable to both human and canine patients.

14 Claims, 12 Drawing Sheets

(56) References Cited

U.S. PATENT DOCUMENTS

| | | | |
|---|---|---|---|
| 2005/0065606 A1* | 3/2005 | Jackson | A61F 2/446 623/17.11 |
| 2007/0233145 A1 | 10/2007 | Richardson | |
| 2009/0157190 A1 | 6/2009 | Collazo | |
| 2010/0076564 A1 | 3/2010 | Schilling | |

* cited by examiner

TIBIAL TUBEROSITY ADVANCEMENT CAGE FOR ACL INJURIES

CROSS REFERENCE TO RELATED APPLICATIONS

This application is a U.S. national phase application, filed in accordance with 35 U.S.C. §371, of International Application No. PCT/IB2013/001577, filed May 30, 2013, which claims the benefit of the filing date of U.S. Provisional Application No. 61/653,077, which was filed May 30, 2012.

FIELD OF THE INVENTION

The invention relates to methods and implants to treat a knee with an injured (e.g., ruptured) anterior cruciate ligament.

BACKGROUND

The Anterior Cruciate Ligament (ACL) in the human knee joint, commonly called Cranial Cruciate Ligament (CrCL) in the canine stifle, is frequently torn in trauma. It also frequently fails, particularly in dogs, after a degenerative process of still unknown etiology.

In human orthopedics, the standard procedure calls for replacement by an ACL allograft, a part of the patient's own patellar tendon, or a part of the tendon removed from the hamstring muscle. The procedure results in a stable knee, but the long-term performance is often unsatisfactory—75 to 90% of cases result in arthrosis of the joint within 15 years of the procedure.

In dogs, the standard procedure is either an extra capsular suture or one of several geometry modifying surgical techniques. In the extra capsular procedure, a suture is placed outside of the joint, usually on the lateral side, to approximate the function of the ligament. The intention of the suture is to provide stability of the joint for several weeks while waiting for fibrosis to form around the joint. The fibrosis should provide for long-term stability. However, the extra capsular suture technique regularly results in failure. Arthrosis of the joint, at a year or so, is the rule rather than the exception.

In surgical techniques, the tibia is cut and a segment of it is repositioned to change the geometry in order to stabilize the stifle. Various techniques have been used including: tibial plateau leveling osteotomy (TPLO; Slocum and Slocum, "Tibial Plateau Leveling Osteotomy For Repair Of Cranial Cruciate Ligament Rupture In The Canine", *Vet. Clin. North Am.* 23:777-795, 1993), cranial closing wedge osteotomy (CWO; Slocum and Devine, "Cranial Tibial Wedge Osteotomy: A Technique For Eliminating Cranial Tibial Thrust In Cranial Cruciate Ligament Repair", *J. Am. Vet. Med. Assoc.* 184:564-569, 1984), and tibial tuberosity advancement (TTA; Tepic et al., "Biomechanics Of The Stifle Joint", in *Proceedings of the 1st World Orthopaedic Vet. Congress*, Munich, Germany, September 2002, pp 189-190). Of the surgical approaches used in dogs, TTA seems to be associated with less morbidity and faster recovery, while providing immediate and durable stability to the joint. Nevertheless, surgical complications are not uncommon with each of these techniques.

Intra-articular prostheses are also occasionally used in dogs and, currently, only on an experimental basis in humans. Again, they require highly invasive procedures to insert them within the stifle. Even then, they generally end in failure.

SUMMARY OF THE INVENTION

This invention provides a solution for a less invasive stabilization of a knee joint in mammals, including dogs and humans, by cranially (anteriorly) advancing the patellar tendon at its insertion to the tibia, much as is done in TTA, but with fewer implants and simpler surgery. According to one aspect of the invention, a wedge-shaped cage is configured to be placed between the partially osteotomized tibial tuberosity and the tibia. The cage is sized and shaped to alter the orientation of the patellar tendon by a predetermined amount. The alteration stabilizes the knee joint, which has been weakened by an ACL (or CrCL) failure. The cage may be made from an artificial material, for example metal (e.g., titanium, a titanium alloy, stainless steel or a cobalt chromium alloy), a polymer (e.g. PEEK or fiber reinforced PEEK, polylactic acid, PLA, polyglycolic acid, PGA, similar resorbable polymers and co-polymers thereof), or a ceramic that is either stable in the body (such as zirconia or alumina) or resorbable (such as tricalcium phosphate or hydroxyapatite). The wedge-shaped cage can include means to allow for effective transfer of shear at its interface to the bone, and the surfaces of the cage facing the bone can be treated to result in high friction or mechanical interlock and to favor intimate bone apposition or ingrowth. The material for the cage should in all circumstances be biocompatible (e.g., non-toxic).

In some embodiments, the wedge-shaped cage is configured to alter the angle of the patellar tendon relative to the common tangent plane set between the condyles of the femur and the condyles of the tibia. This angle is decreased between about 10 degrees and about 15 degrees for dogs and between about 10 degrees and about 30 degrees in humans. The angle of the patellar tendon relative to the common tangent can be approximately 90 degrees when the knee is extended.

According to another aspect of the invention, a procedure provides stabilization of the knee joint caused by failure of the ACL or CrCL. The procedure includes moving the patellar tendon away from the tibia together with its tibial insertion. A wedge-shaped cage is inserted between the partially osteotomized tibial tuberosity and the tibia and optionally fixed to either the tibia or to both the tibia and the tibial tuberosity. The procedure can include altering the angle of the patellar tendon relative to the common tangent of the knee joint.

7(a) through 7(i) are illustrations of the compositions described herein and of the insertion of a cage as described herein into the knee joint of a subject.

DETAILED DESCRIPTION

The present invention provides a cage and a procedure for adjusting the position and angle of the patellar tendon in order to stabilize the knee. The knee is stabilized through geometric changes similar to those achieved by TTA in a less invasive procedure. The TTA procedure is explained in connection with FIG. 1 to illustrate stabilization of the knee. The TTA procedure is currently accepted as a standard treatment for ruptured ACL in dogs (Fossum, "Small Animal Surgery", Elsevier Health Sciences, 3$^{rd}$ edition, 2007; Boudrieau, "Tibial Plateau Leveling Osteotomy Or Tibial Tuberosity Advancement?", *Vet. Surg.* 38:1-22, 2009).

Figure 1:
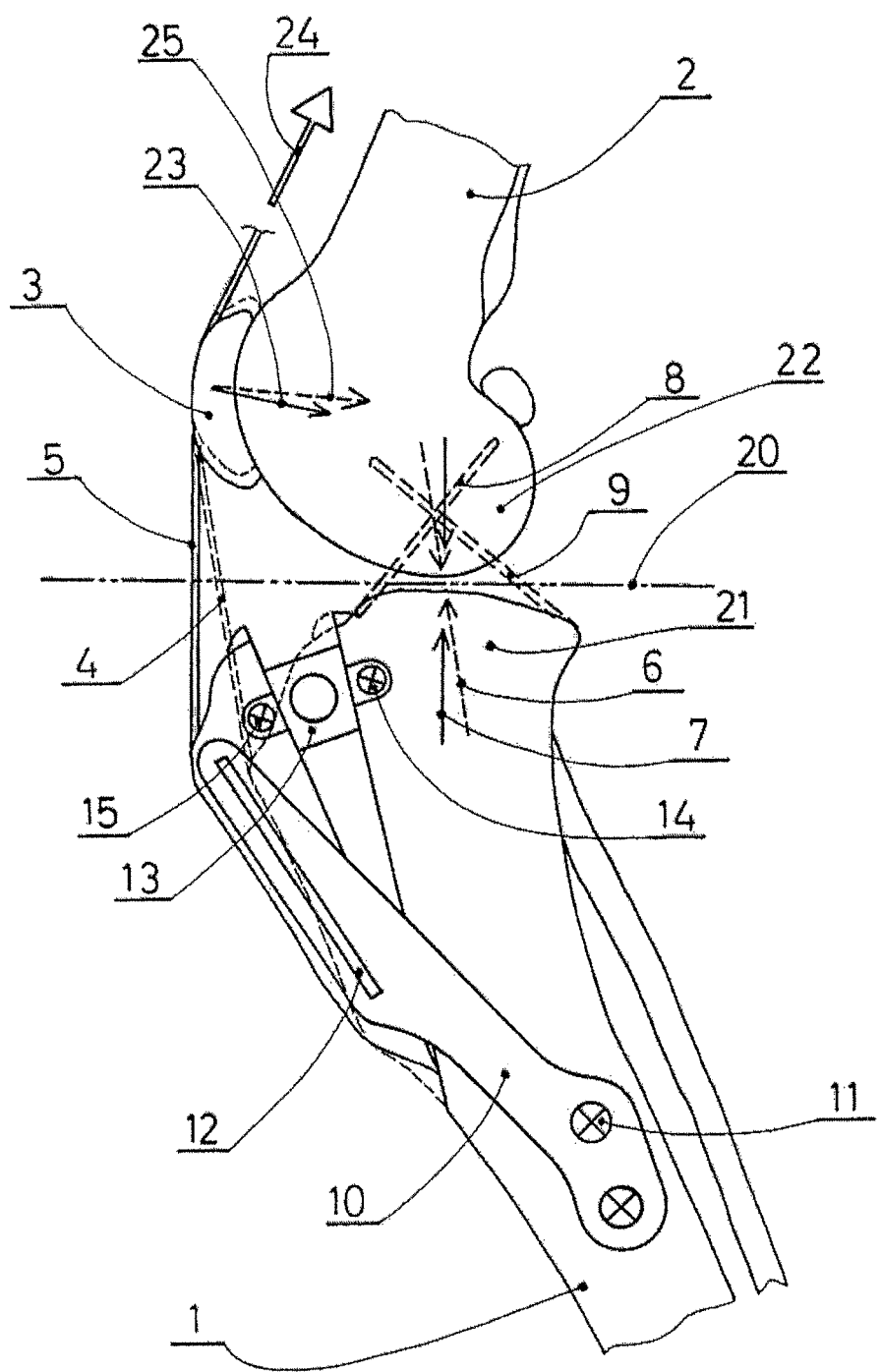
FIG. 1 is a side view of a canine knee joint (stifle) on which the TTA procedure has been performed.

FIG. 1 illustrates the knee joint and the positions of certain structures and forces both before and after the TTA procedure. The tibia 1 and the femur 2 articulate at the knee joint via condyles of the femur 22 and condyles of the tibia 21, divided by a plane which is referred to as the common tangent 20. When carefully examined, the medial and the lateral condyles will have different common tangents, but in practice those are usually approximated by a single planar surface 20. Pull 24 from the quadriceps muscles acts on the patella 3, which in turn pulls the tibia via the patellar tendon 5 (4 in its original orientation). The force between the condyles of the femur and the tibia is approximately parallel to the patellar tendon 5, having been tilted from its original orientation 6 before the advancement (which was parallel to 4) into the new orientation 7, which is perpendicular to the common tangent plane 20. When the joint force 7 is perpendicular to the common tangent plane 20, neither the cranial (anterior) ligament 8 nor the caudal (posterior) cruciate ligament 9 are needed to stabilize the joint. When this condition is satisfied in the extended position of the knee, such as shown on FIG. 1, the joint will also be stable when flexed, as stability is provided by the caudal (posterior) cruciate ligament 9.

Advancement of the tuberosity, after an opening wedge osteotomy, is maintained by a cage 13 fixed to the tibia with a caudal screw 14 and a cranial screw 15. The tension of the patellar tendon 5 is transferred to the body of the tibia via a tension-band plate 10, fixed distally to the tibia with screws 11, and proximally to the tuberosity with a fork 12.

In addition to balancing the internal force 7 of the knee joint, TTA also reduces the force 23 (originally 25) between the patella and the femur. A procedure similar to TTA has been invented and performed in human surgery as well by Maquet ("Advancement Of The Tibial Tuberosity", *Clin. Orthop. Rel. Res.* 115:225-230, 1976) in order to reduce the patello-femoral joint force in cases of arthrosis of that joint. There is no indication that Maquet's procedure has ever been performed for ruptured anterior cruciate ligament in a human (personal communication with Dr. Maquet).

The procedure of the present invention provides changes similar to those of TTA without the need to fully cut and reattach the tuberosity. The advantages of the invention are obtained through placement of a wedge-shaped cage between the tibia and the tibial tuberosity, the cage being specifically designed to facilitate transfer of shear forces and thus diminish the tension force that needs to be transferred via bone attachment at the distal end of the partial osteotomy.

Figure 2:
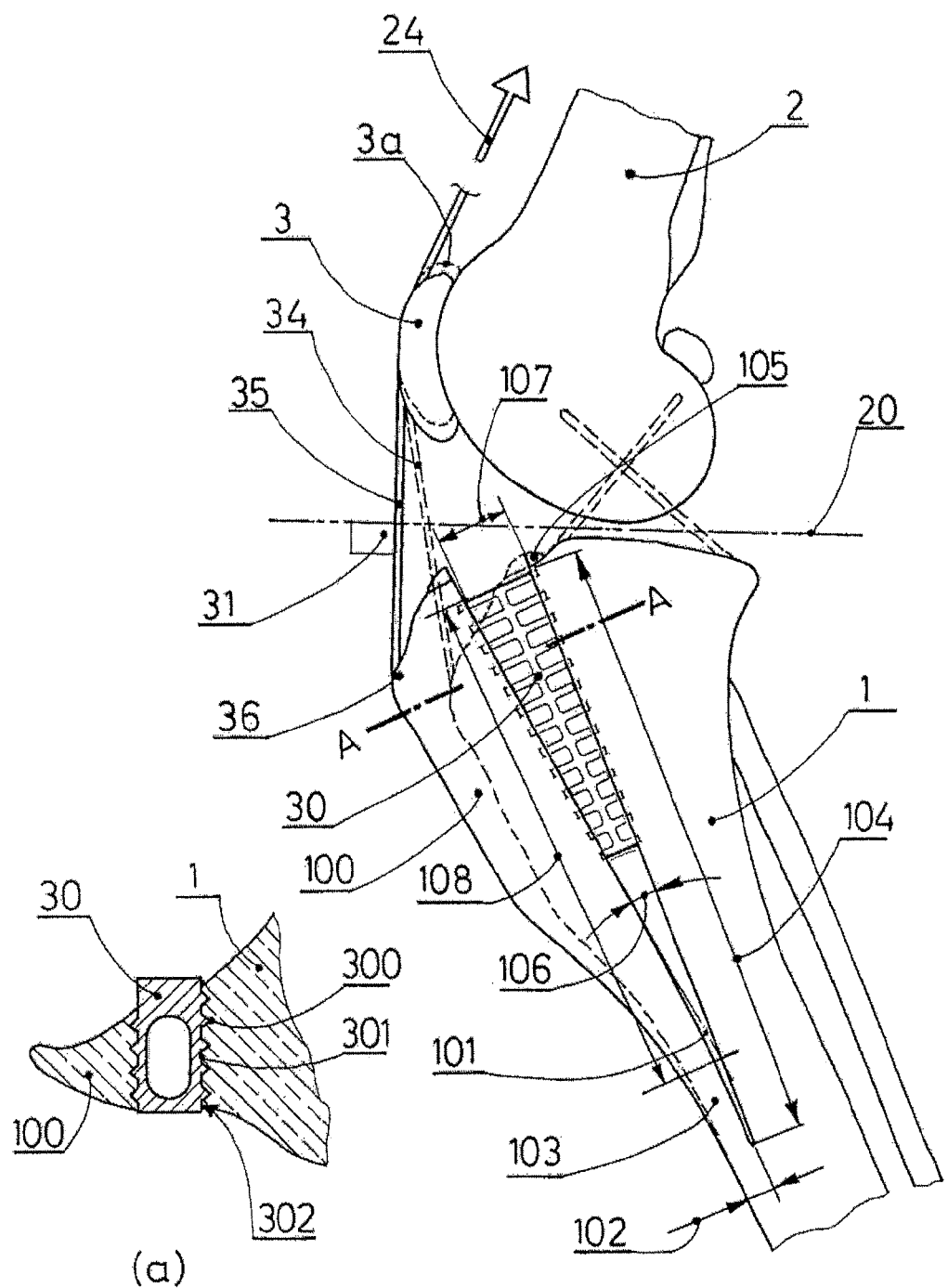
FIG. 2 is a side view of a canine knee joint having a tibial tuberosity advanced by a wedge-shaped cage according to an embodiment of the invention.

FIG. 2 shows a side or medio-lateral view of a canine knee in the extended position with a wedge-shaped cage 30 of the present invention. The patellar tendon has been rotated from its original position 34 to a new position 35 by insertion of a cage 30 between the partially ostotomized tibial tuberosity 100 and the tibia 1. The insertion point 36 of the tendon 35 (34) to the tibia 1 is moved cranially. The angle 31 between the patellar tendon 35 and the common tangent plane 20 should be about 90 degrees (e.g., from about 86 to about 91 degrees). To provide a margin of safety, the angle can be slightly less than 90 degrees (e.g., about 88 degrees) when the knee is extended to keep the knee stable. In dogs, this calls for an average rotation of the patellar tendon on the order of 10 to 15 degrees; in humans, a larger correction of 10 to 30 degrees is needed for a full compensation of a ruptured ACL. The length 104 of the partial osteotomy 101 and the distance 102 from the cranial aspect of the cortex at its distal end are of crucial importance in minimizing the risk of fracturing the remaining bone attachment 103. There are four conditions that the osteotomy position and length preferably satisfy: (i) the attachment needs to flexible enough to allow for opening the wedge without fracturing; (ii) the attachment needs to be strong enough to transfer longitudinal tension remaining after most of the patellar tendon pull has been transferred to the body of the tibia via the cage; (iii) the attachment has to be strong enough to favor longitudinal crack propagation at the end of the osteotomy over a transverse crack (this is only possible due to high anisotropy of the bone with the longitudinal strength about an order of magnitude higher than the transverse strength); and (iv) the attachment has to be strong enough to resist fracture due to transverse forces generated by the moment of the patellar tendon pull around the cranial proximal edge of the cage. Finite element analysis and experiments with dog tibias suggest that the optimal distance 102 is just about equal to the thickness of the cranial cortex and that a wedge angle 106 of 6 to 10 degrees, preferably of about 8 degrees, can be safely opened with the length 104 of the osteotomy 5 to 15 mm longer than the theoretical length 108, whereby L108=Ltheoretical=[½ Gap 107]/tan(½ of angle 106). At the proximal end, the osteotomy should be placed at or slightly cranial to the tuber of Gerdy 105 in order to provide optimal bony support for the cage.

FIG. 2a shows a cross-section through the wedge-shaped cage 30, the tibia 1 and the tibial tuberosity 100. The cage should preferably be provided by grooves 301 and spikes 300 and generally rough surfaces 302 facing the bone so as to allow for shear transfer with minimal slippage.

With the intact remaining attachment 103, under the same pull of the quadriceps 24, the patella 3 will sit slightly displaced distally from its original position marked as 3a. However, this will not affect its function.

Figure 3:
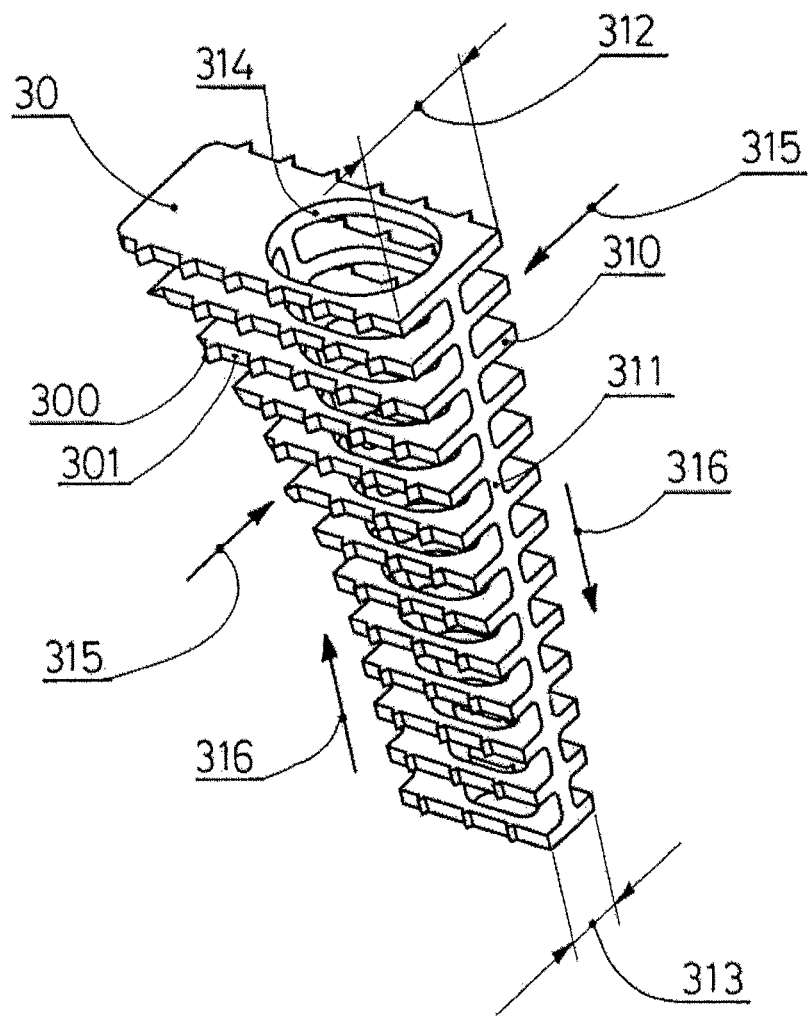
FIG. 3 is a perspective view from the medial side of the wedge-shaped cage according to an embodiment of the invention.

FIG. 3 shows a perspective view of a wedge-shaped cage 30 according to an embodiment of the invention. A plurality of horizontally oriented ribs 310 are connected by a centrally located spine 311. The width 312 of the ribs at the proximal end of the cage is larger than the width 313 at the distal end, giving the cage its wedge shape. The ribs 310 are provided with openings 314 running the full length of the cage, their size gradually decreasing distally. The basic function of the cage is to transfer compression denoted by arrows 315 and shear denoted by arrows 316, while allowing the bone to grow through the cage with minimal impediment. Spikes 300 alternate with grooves 301 along the bone facing edges of the ribs 310. All of the surfaces that may contact the bone are rough blasted, preferably with roughness of Ra of about 3 to about 5 micrometers. Preferred material for the cage is c.p. titanium, or an alloy of titanium such as TiAl6V4 or TiAl6Nb7. Bone conductive or bone inductive surface treatments are desired, but optional. If the metal of the cage is titanium, or an alloy of titanium, surface treatments can be one of: pickling, anodizing, glow discharge anodizing with addition of calcium phosphate, plasma coating with porous titanium or with hydroxyapatite.

Figure 3A:
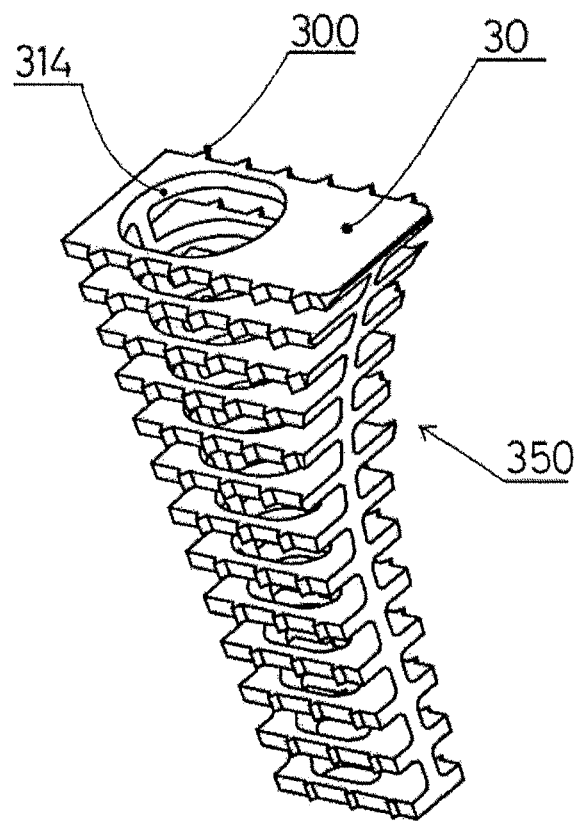
FIGS. 3a and 3b are perspective views from the lateral side of the wedge-shaped cage according to an embodiment of the invention.
Figure 3B:
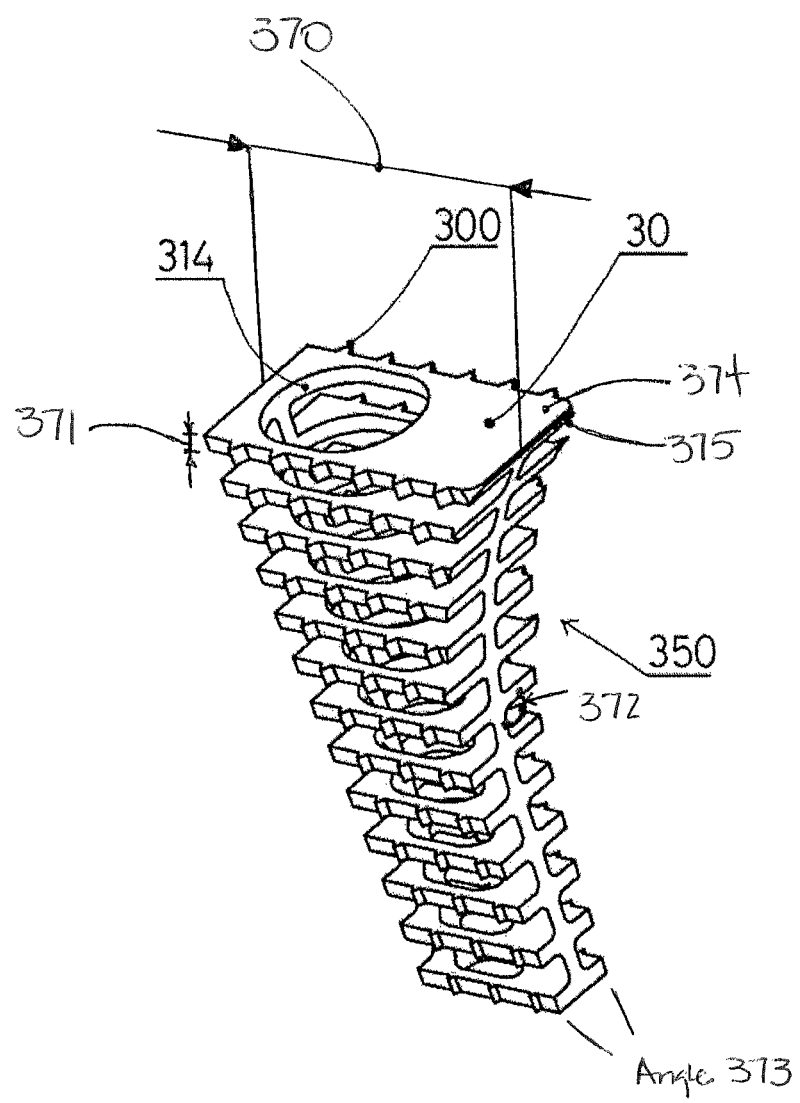

FIG. 3a shows the cage 30 from its lateral side 350, curved to better fit the anatomical shape of the tibial tuberosity. FIG. 3b shows cage 30 from its lateral side 350. The length of the rib 370, the thickness of the rib 371, the angle between the spine and a rib extending therefrom 372, the angle of the wedge-shaped cage 373, the upper planar surface of a rib 374, and the lower planar surface of a rib 375 are illustrated.

Figure 4:
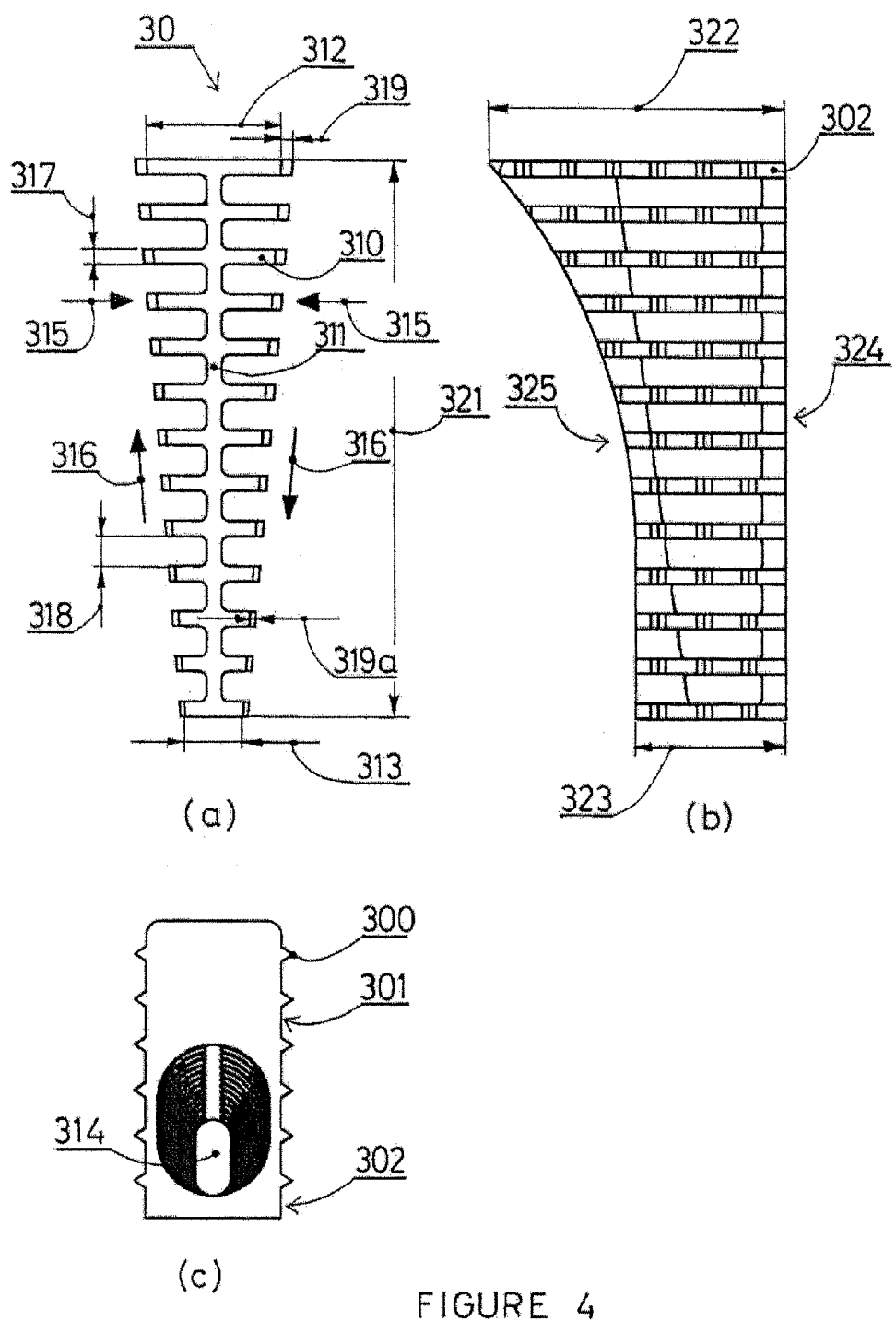
FIGS. 4a-4c are orthogonal views of the wedge-shaped cage according to an embodiment of the invention.

FIG. 4 shows orthogonal views of the wedge-shaped cage 30 according to an embodiment of the invention. FIG. 4a is the view corresponding to the sagittal plane of the tibia, i.e. the view from medial to lateral when implanted. The ribs 310 are spaced apart along the spine 311, their thickness denoted by 317 and the distance between them by 318. In general, it is desirable to have the distance 318 larger than the thickness 317. Experience from use of conventional TTA cages in dogs suggests that a ratio of 1.5 to 3, preferably about 2, is a good compromise in providing sufficient support for the bone and yet leaving a lot of room for bone to grow through the cage. The thickness of the spine 311 should be about the same as the thickness of the ribs 310. Preferred range for the rib thickness is about 0.7 to about 1.5 mm, most preferably about 1 mm. A preferred range for the distance between the ribs is about 1 to about 4 mm, most preferably about 2 mm. The width of the ribs 310 at the proximal (top) end of the cage denoted by 312 for use in dogs is generally in the range of about 3 to about 15 mm, depending on the size of the dog and the anatomical features of the stifle. The width of the cage at the distal (bottom) end of the cage 313 depends on the angle 106 (shown on FIG. 2) of the cage and its length 321. Preferred range of the angle 106 is about 6 to about 10 degrees, most preferably about 8 degrees. Design of the cage as disclosed offers a great flexibility in providing the cage with sufficient strength to resist compressive loading denoted by arrows 315 as well as shear loading denoted by arrows 316 without mechanical failure, yet offering a good degree of compliance, especially when loaded in shear 316, so that the loading is distributed along the length 321 of the cage. A solid cage, or one made from bulk porous metal does not allow for sufficient control of compliance needed to provide a favorable load distribution to adjacent bone. This may lead to stress concentrations and local bone resorption of the bone at interfaces to the cage.

The depth 319 of the spikes 300 at the proximal end of the cage is in the range of about 0.5 to about 1.5 mm. While larger spikes may provide stronger anchorage in the bone, they also require wider opening of the osteotomy to fit before being pushed into the bone, which may lead to cracking of the bone attachment distally. By experiment, the spike depth of about 0.7 to about 1 mm has been found to offer a good compromise between stability and gap opening needed to insert the cage. The depth of the spikes decreases distally, shown as 319a, to avoid excessive opening of the osteotomy at insertion of the implant.

FIG. 4b shows the cage view corresponding to the frontal (anterior to posterior) plane of the tibia. The depth 322 of the cage at the proximal end is significantly greater than the depth 323 at the distal end, so that the cage approximates the anatomical shape of the tibia at the plane of the osteotomy. The medial face of the cage is denoted as 324; the lateral, curved face, is denoted by 325.

FIG. 4c is the top view of the cage 30, showing plurality of the openings 314 decreasing in size from proximal to distal. The spikes 300 are positioned so as to leave an area of the ribs 310 at the medial and the lateral ends flat, 302, just roughened—the hard cortical bone would not be penetrated by spikes without extreme pressure and possible damage.

Figure 5:
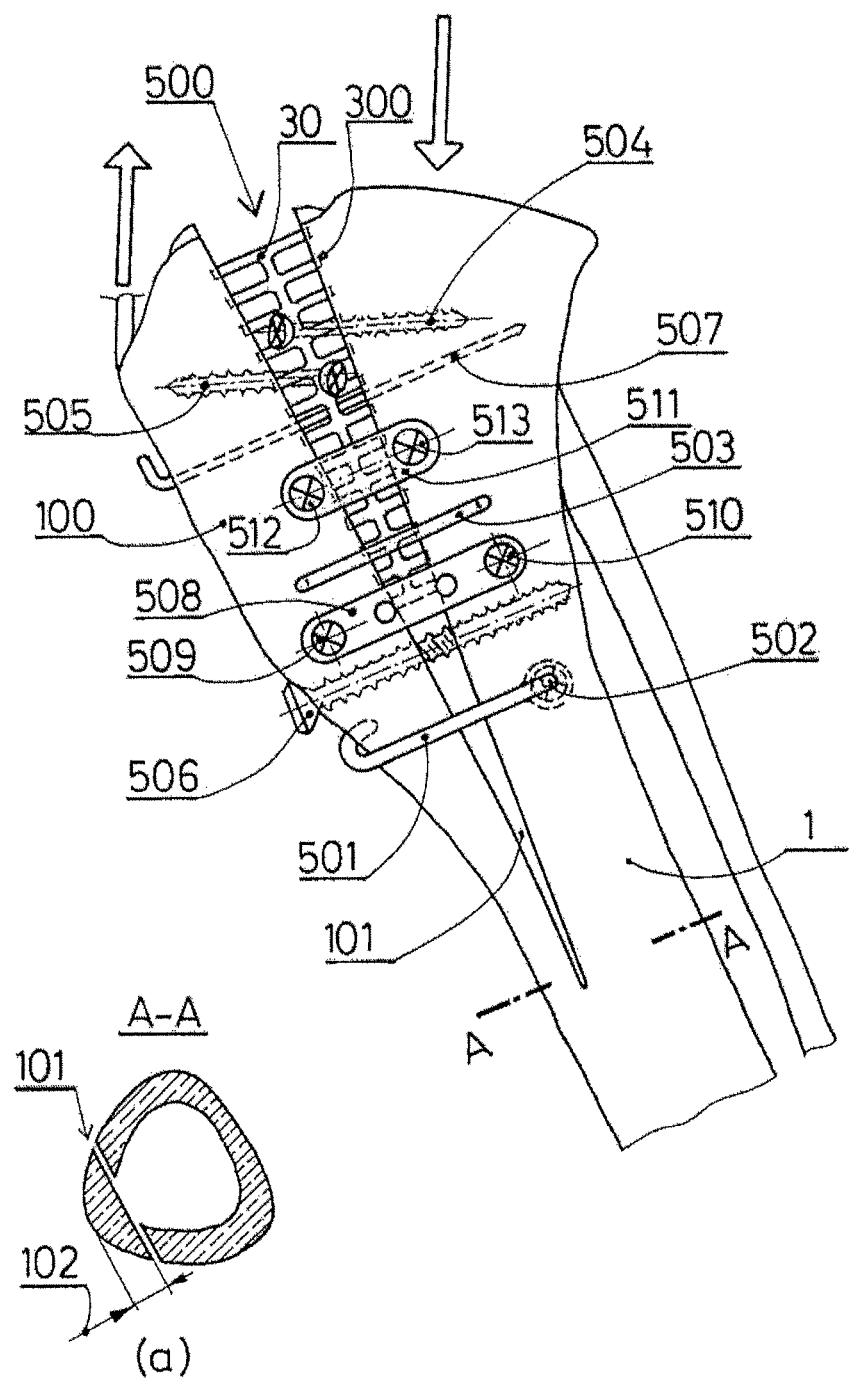
FIG. 5 is a side view of a canine tibia with a wedge-shaped cage according to an embodiment of the invention with optional, additional means of stabilization.

FIG. 5 shows a medial view of the tibia 1 with a wedge-shaped cage 30 inserted into the gap 500 of the partial osteotomy 101, cut to separate the tibial tuberosity 100 from the rest of the tibia 1. While spikes 300 in most cases are sufficient to stabilize the cage 30 in the gap 500 and provide for the shear transfer across the cage, in certain cases it may be necessary to provide further means for stabilization of the cage. Several options are shown here.

A hook-shaped implant 501 can be used to pull the tibial tuberosity 100 towards the rest of the tibia just distally to the cage 30. The hook may be made to engage the tibia 1 directly by a bent end, or it may be fixed to the tibia 1 by an additional screw 502.

A conventional screw 506 may also be used for the same purpose. Again, the ideal position for that screw is just distal to the cage 30, but it may also be inserted through the cage between its ribs 310.

Another possibility is to use a bone staple 503 from the tuberosity 100 over the cage 30 and into the bone of the tibia 1.

Yet another means of fixation is by a pair of screws 504 and 505, inserted between the ribs of the cage in an oblique direction fixing the cage to the tibia 1 and the tuberosity 100, respectively. These screws enter the bone through the osteotomy plane, leaving the medial cortex intact.

Most common technique in similar surgical procedures, e.g. tuberosity transposition for patellar luxations, is to use a pin 507 placed through the tuberosity 100 through the cage 30 into the tibia 1. This particular placement of stabilization pin is the least desirable since it increases the risk of tuberosity fracture. The cranial hook of the pin 507 may be used as an anchor for figure-8 wire, as is commonly done in similar situations.

Yet another embodiment of the supplemental fixation is by means of a bone plate 508 spanning the gap and fixed to the tuberosity by at least one screw 509 and to the tibia by at least one screw 510. The plate 508 can also be fixed to the cage itself and thus act as the flange of the conventional TTA implant.

Another embodiment of the supplemental fixation is via a flange 511 of the type used in the original TTA cage, fixed to the bone by screws 512 and 513. The flange 511 may be fixed to the cage 30, or it may just bridge over it.

Figure 6:
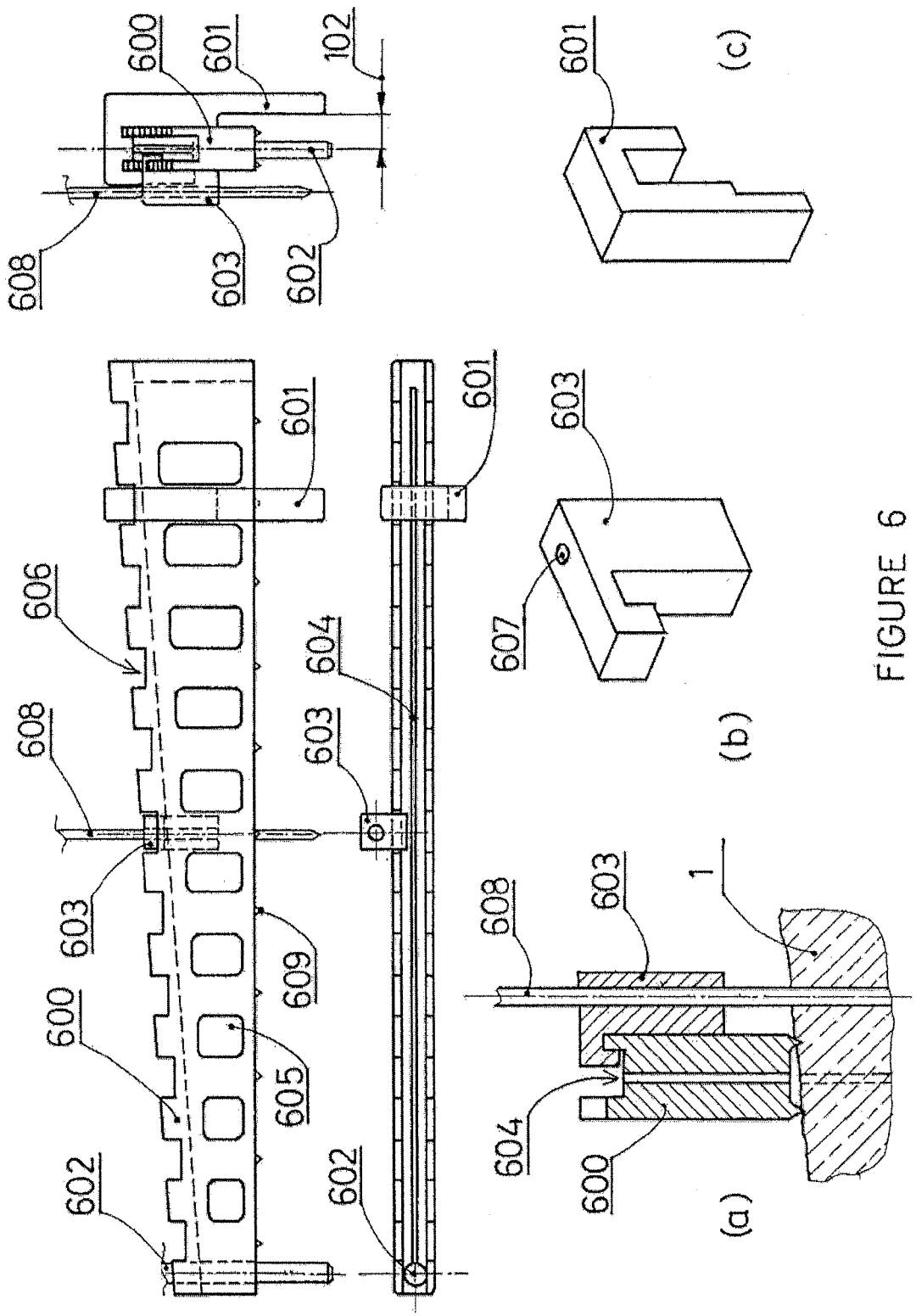
FIG. 6 shows a saw guide specifically adapted for performing the osteotomy according to the invention. FIGS.
Figure 7A:
Figure 7B:
Figure 7C:
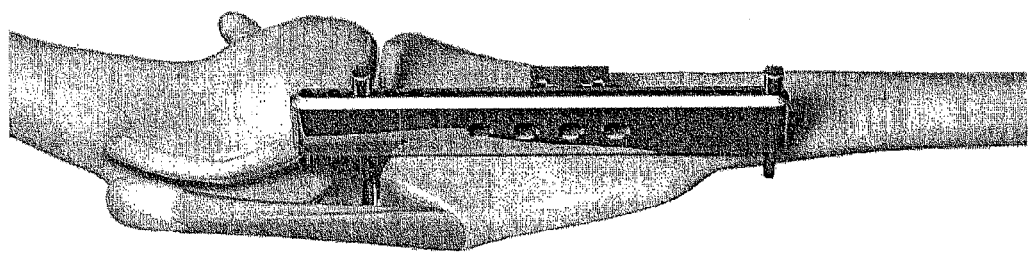
Figure 7D:
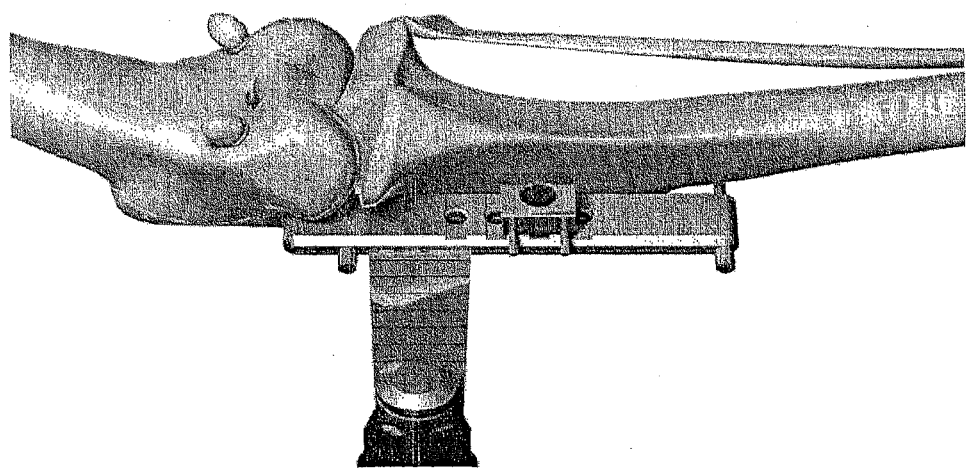
Figure 7E:
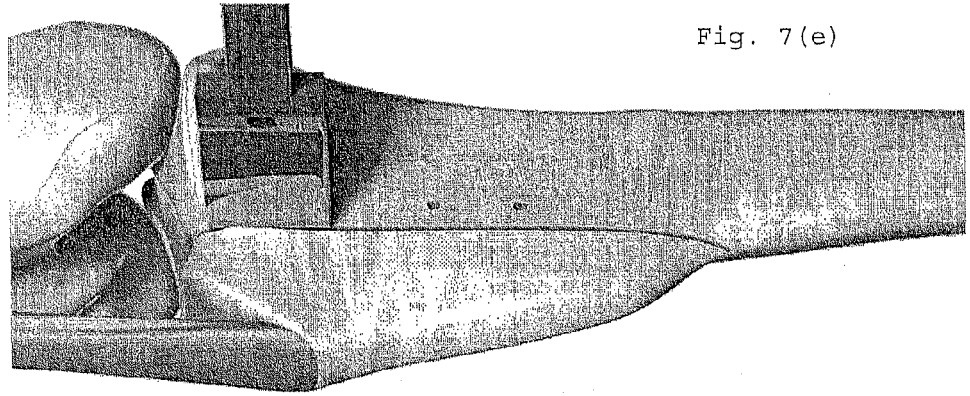
Figure 7F:
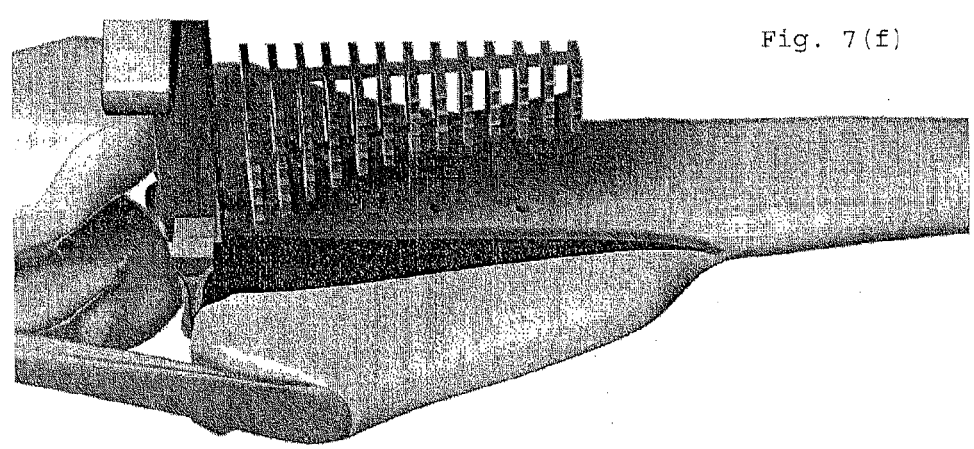
Figure 7G:
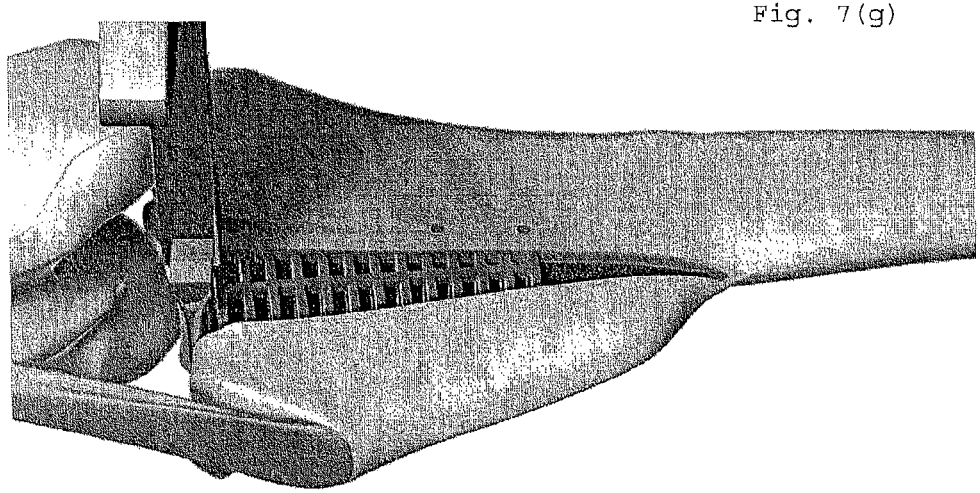
Figure 7H:
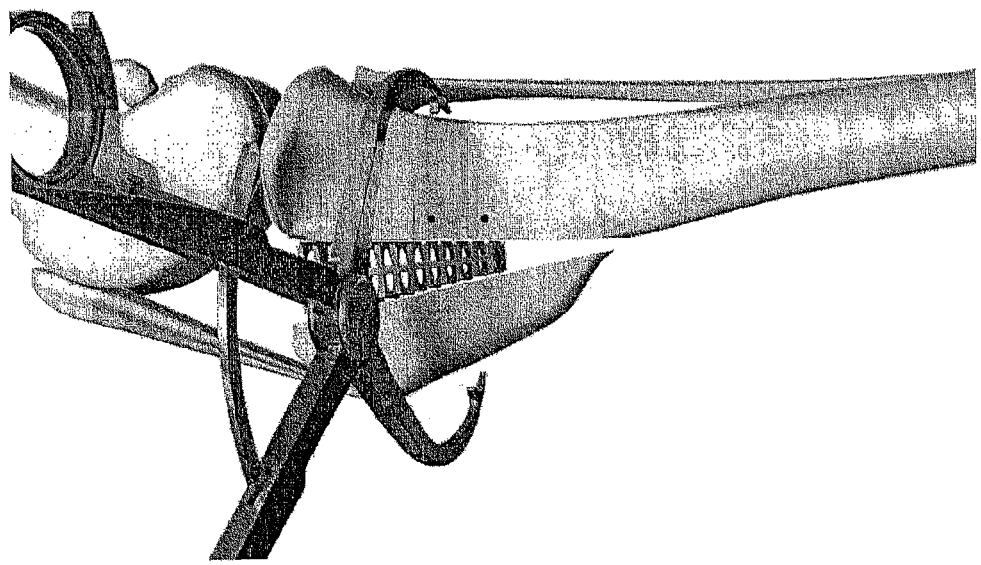
Figure 7I:
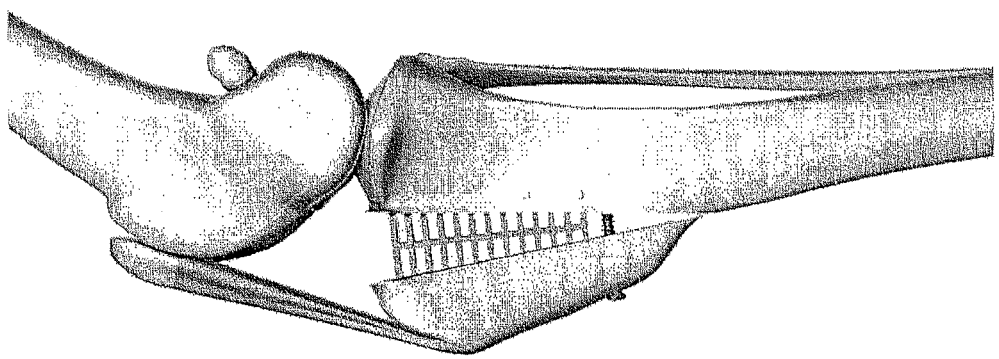

FIG. 6 shows a saw guide 600 specifically designed to facilitate execution of the partial osteotomy 101 according to this invention. A clip-on gauge/spacer 601 is used distally to define the position of the guide needed to place the saw cut at the pre-determined distance 102 from the cranial cortex to the saw cut. For dog tibias the gauges/spacers are provided with distances from about 2 to about 5 mm in 0.5 mm increments.

Proximally, a pin 602 is used to position the osteotomy cut over the tuber of Gerdy, safely in front of the meniscus. The pin is inserted into the joint through a small medial incision of the joint capsule.

The saw guide is then fixed to the body of the tibia 1, by a temporary pin 608, passed through the hole 607 in the clamp 603. Both the clamp 603 and the gauge/spacer 601 can be placed into any of the grooves 606 along the length of the guide 600. The saw is guided by a cutout 604 in the saw guide 600. Side windows 605 provide for effective flushing of the saw and allow for visual control of the process. Grooves 606 are marked with the length of the cut measured from the pin 602, and thus allow for placing of the gauge/spacer 601 at the proper position defining the predetermined length of the osteotomy.

While the primary indication of the invention is rupture of the ACL in human or CrCL in dog, it can also be used for partial ruptures of the same. It may also be used as a supportive measure for ACL repairs, as well as for intra-articular prosthesis or extra-articular sutures. It can also be used as a substitute for Maquet procedure for patello-femoral joint arthrosis. Cages produced from artificial, biocompatible materials have advantages in terms of convenience of use and selection of sizes.

The procedure of the present invention includes advancing the insertion of the patellar tendon to alter the relative angle with the tibial plateau or the common tangent of the joint. In an embodiment of the invention, the patellar tendon is advanced so that the relative angle with the tibial plateau or the common tangent of the femoro-tibial joint is approximately 90 degrees, or slightly less, e.g. about 88 degrees, when the knee is extended. In another embodiment of the invention, the patellar tendon is advanced so that the angle is decreased in the range of 10 to 30 degrees. In another embodiment of the invention, the patellar tendon is advanced so that the angle is decreased in the range of 10 to 15 degrees for a dog. In another embodiment of the invention, the patellar tendon is advanced so that the angle is decreased in the range of 10 to 30 degrees for a human. The patellar tendon is advanced by inserting a wedge-shaped cage between the partially osteotomized tibial tuberosity and the tibia. The cage may be placed into the plane of the osteotomy and stabilized by its bone-penetrating spikes alone, or it may be fixed by additional means such as screws, pins, plates, flanges, hooks, wires or staples.

Having disclosed at least one embodiment of the present invention, various adaptations, modifications, additions, and improvements will be readily apparent to those of ordinary skill in the art. Such adaptations, modifications, additions and improvements are considered part of the invention.

In particular embodiments, the invention features a cage for use in treating an injured anterior cruciate ligament. The cage can include: an elongated spine having a proximal end and a distal end; a plurality of ribs, each rib extending laterally from the elongated spine and terminating in first and second side surfaces that define the thickness of the rib; and a plurality of spikes extending from the first and/or second side surfaces of each rib. The plurality of ribs can extend laterally from the elongated spine at roughly equal intervals from the proximal end of the elongated spine to the distal end of the elongated spine. The distance between the ribs can be equal to or larger than the thickness of the ribs. The ratio of the distance between the ribs to the thickness of the ribs can be about 2:1. The spine can have a thickness that is equal to or greater than the thickness of the ribs. The thickness of the ribs can be about 0.7 to about 1.5 mm; the distance between the ribs can be about 1 to about 4 mm; the width of rib at the proximal end of the elongated spine can be about 3 to about 15 mm; and/or the plurality of spikes can extend about 0.5 to about 1.5 mm from the side surfaces. Each rib can have a length and a width defining a planar surface and the length and/or width of the rib at the proximal end of the elongated spine can be greater than the respective length and/or width of the rib at the distal end of the elongated spine. For example, the planar surface of each rib can include an opening and the openings can be aligned to generate a tunnel through the long axis of the cag. The width of the ribs can progressively narrow from the proximal end to the distal end of the cage, thereby generating a wedge-shaped cage. The angle of the wedge-shaped cage can be about 1 to about 15 degrees (e.g., about 5 or 6 degrees to about 9 to 12 degrees and figures in between). 1. At least 50% (e.g., at least about 60%, 70%, 75%, 80%, 85%, 90% or 95% of the volume within the cage can be free volume. The first side surfaces can align with one another to generate a curved lateral face and the second side surfaces can align with one another to generate a straight medial face. The curve of the curved lateral face can mimic the curve of the tibial tuberosity. The cage can have a roughened surface (e.g., the surface of the spikes and/or grooves therebetween can be roughened). The roughened surface can have variations of about 3 to about 5 micrometers. The cage can be fashioned from or can include titanium or an alloy thereof. A surface of the cage (any one or more of those described herein) can be treated by pickling or anodizing (e.g., by flow discharge anodizing with the addition of calcium phosphate, plasma coating with porous titanium or with hydroxyapatite). The invention also features a procedure for treating a subject having an injured anterior cruciate ligament. The procedure can be carried out by fully or partially ostotomizing a tibial tuberosity to produce a full or partial osteotomy and inserting a cage as described herein into the site of the osteotomy. The procedure can include the steps that produce the result illustrated by FIGS. 7(c) through 7(h). The invention also features method of making a cage as described herein by machining a metal-containing substrate into the form of the cage. The invention also features a kit comprising a cage as described herein and instructions for use (e.g., written, visual, or audiovisual instructions). The kit can further include an ancillary device as described herein useful in the implantation of the cage. In the implantation procedure, the angle between the patellar tendon and a common tangent plane can be from about 86 to about 91 degrees; the angle between the patellar tendon and a common tangent plan is between about 88 and 90 degrees when extended; the patellar tendon can have an average rotation on the order of about 10 to about 30 degrees. In the procedure, the theoretical length of the partial osteotomy can be calculated as [½ G]/tan (½ A), wherein G is the gap at the proximal end of the osteotomy between the tibial tuberosity and the tibia and A is the wedge angle. The length of the partial osteotomy can be about 5 to about 15 mm longer than is theoretical length. In the procedure, one can employ a hook-shaped implant to pull the tibial tuberosity toward the tibia, and the procedure can further include fixing the hook-shaped implant with a screw. As noted, the spine can be elongated, and we may refer to the cage as a surgical cage configured for use in ACL repair; with dimensions suitable for implantation at a knee joint (e.g., adjacent the tibia) of a subject. The subject can be a mammal (e.g., a human, a domesticated animal (e.g., a dog or cat) or a farm animal (e.g., a horse)). The components or elements described within the present cage can be contiguous or non-contiguous. For example, a spike can extend from a rib with no defined or discernible joint between the spike and the rib. "Roughly equal" means "about the same." For example, two elements are roughly equal when they vary from one another by no more than 10% with respect to a defined aspect or characteristic. For example, ribs extending from the elongated spine extend at roughly equal intervals when the distance between one rib and the next varies by no more than 10%. "About" can also mean within 10% (±10%). The angle between the spine and the ribs extending therefrom can be about 90 degrees. The spikes can progressively narrow as they protrude away from the rib (toward the outermost periphery of the cage). The spikes define a groove therebetween. Where each rib has a length and a width defining a planar surface, each rib can also have an upper and a lower planar surface.

What is claimed is:

1. A cage for use in treating an injured anterior cruciate ligament, the cage comprising:
   an elongated spine having a proximal end and a distal end;
   a plurality of ribs, each rib extending laterally from the elongated spine and terminating in first and second side surfaces that define the thickness of the rib, wherein each rib has a length and a width defining a planar surface, and wherein the width, the length, or the width and the length of the ribs progressively narrow from the proximal end to the distal end of the elongated spine, thereby generating a wedge-shaped cage; and
   a plurality of spikes extending from the first side surfaces, the second side surfaces, or the first and second side surfaces of each rib.

2. The cage of claim 1, wherein the plurality of ribs extend laterally from the elongated spine at roughly equal intervals from the proximal end of the elongated spine to the distal end of the elongated spine.

3. The cage of claim 2, wherein the distance between the ribs is equal to or larger than the thickness of the ribs.

4. The cage of claim 2, wherein the ratio of the distance between the ribs to the thickness of the ribs is about 2:1.

5. The cage of claim 1, wherein the spine has a thickness that is equal to or greater than the thickness of the ribs.

6. The cage of claim 1, wherein the thickness of the ribs is about 0.7 to about 1.5 mm; the distance between the ribs is about 1 to about 4 mm; the width of the rib at the proximal end of the elongated spine is about 3 to about 15 mm; and/or the plurality of spikes extend about 0.5 to about 1.5 mm from the side surfaces.

7. The cage of claim 1, wherein the planar surface of each rib comprises an opening and the openings are aligned to generate a tunnel through the long axis of the cage.

8. The cage of claim 7, wherein the angle of the wedge-shaped cage is about 6 to about 10 degrees.

9. The cage of claim 1, wherein at least 70% of the volume within the cage is free volume.

10. The cage of claim 1, wherein the first side surfaces align with one another to generate a curved lateral face and the second side surfaces align with one another to generate a straight medial face.

11. The cage of claim 10, wherein the curve of the curved lateral face is configured to mimic the curve of the tibial tuberosity.

12. The cage of claim 1, wherein a surface of the cage has a roughened surface.

13. The cage of claim 12, wherein the surface of the cage comprises a surface of the spikes and/or a plurality of grooves therebetween.

14. The cage of claim 1, wherein the cage comprises titanium or an alloy thereof, a resorbable polymer, or a resorbable ceramic.

* * * * *